(12) United States Patent
Weitkemper et al.

(10) Patent No.: US 6,444,659 B1
(45) Date of Patent: Sep. 3, 2002

(54) USE OF MIXTURES OF ACTIVE SUBSTANCES, CONTAINING PHYTOSTENOLS AND/OR PHYTOSTENOL ESTERS AND POTENTIATORS, FOR THE PRODUCTION OF HYPOCHOLESTEROLEMIC AGENTS

(75) Inventors: Norbert Weitkemper, Leverkusen; Bernd Fabry, Korschenbroich, both of (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/319,036

(22) PCT Filed: Nov. 19, 1997

(86) PCT No.: PCT/EP97/06450

§ 371 (c)(1),
(2), (4) Date: May 28, 1999

(87) PCT Pub. No.: WO98/23277

PCT Pub. Date: Jun. 4, 1998

(30) Foreign Application Priority Data

Nov. 28, 1996 (DE) .......................................... 196 46 286
Jan. 13, 1997 (DE) .......................................... 197 00 796

(51) Int. Cl.⁷ .......................... A61K 31/56; A61K 9/48; A61K 31/7088; A61K 31/722; A61K 35/78
(52) U.S. Cl. ....................... 514/171; 424/456; 424/725; 514/44; 514/55; 514/169; 514/170; 514/182
(58) Field of Search .................... 424/456, 725; 514/44, 55, 729, 706, 708, 962, 169, 170, 171, 182

(56) References Cited

U.S. PATENT DOCUMENTS

| 3,089,939 A | 5/1963 | Dunlap et al. ................. 219/19 |
| 3,203,862 A | 8/1965 | Jones ........................... 167/65 |
| 4,765,976 A | 8/1988 | Grollier et al. ............... 424/70 |
| 4,833,129 A | * 5/1989 | Kawai et al. .................. 514/44 |
| 5,130,302 A | * 7/1992 | Spielvogel et al. ........... 514/45 |

FOREIGN PATENT DOCUMENTS

| CA | 928 140 | 6/1973 |
| CA | 2 101 079 | 8/1994 |
| DE | 2 035 069 | 1/1971 |
| DE | 3 713 099 | 10/1987 |
| DE | 4 442 987 | 6/1996 |
| DE | 195 37 001 | 3/1997 |
| DE | 196 04 180 | 8/1997 |
| EP | 0 195 311 | 9/1986 |
| EP | 0 289 636 | 11/1988 |
| EP | 0 562 849 | * 9/1993 |
| EP | 0 594 612 | 5/1994 |
| FR | 2 701 266 | 8/1994 |
| WO | WO94/01413 | 1/1994 |

OTHER PUBLICATIONS

Maezaki et al., 'Hypocholesterolemic effect of chitosan in adult males', Biosci. Biotech., Biochem. (1993), vol. 57, No. 9, pp. 1439–1444.*
J. Nutrit., vol. 50, pp. 191–201.
Ullmann's Encyclopedia of Industrial Chemistry, vol. 6, (1986) pp. 231–332.
Happi, vol. 27, (1990) p. 57.
Drug Cosmetic Ind., vol. 148, (1991) pp. 24–30.
Seifen–Ole–Fette–Wachse, vol. 117, (1991) pp. 633–637.
Makromol Chem., vol. 177, (1976) pp. 3589–3600
J.Am.Chem.Soc., vol. 63, (1941) pp.1259–1261.

* cited by examiner

Primary Examiner—Jose' G. Dees
Assistant Examiner—Frank Choi
(74) Attorney, Agent, or Firm—John E. Drach; Glenn E. Murphy; Steven J. Trzaska

(57) ABSTRACT

A hypocholesterolemic composition containing: (a) an active ingredient selected from the group consisting of a phytostenol, a phytostenol ester, and mixtures thereof; and (b) a potentiating agent selected from the group consisting of a chitosan, a phytostenol sulfate, a (deoxy)ribonucleic acid, and mixtures thereof.

20 Claims, No Drawings

USE OF MIXTURES OF ACTIVE SUBSTANCES, CONTAINING PHYTOSTENOLS AND/OR PHYTOSTENOL ESTERS AND POTENTIATORS, FOR THE PRODUCTION OF HYPOCHOLESTEROLEMIC AGENTS

This application is a 371 of PCT/EP97/06450, filed on Nov. 19, 1997.

BACKGROUND OF THE INVENTION

This invention relates to the use of mixtures of phytostenols or phytostenol esters and selected potentiating agents for the production of preparations for reducing the serum cholesterol content of warm-blooded organisms.

Hypocholesterolemic agents are understood to be agents which lead to a reduction in the serum cholesterol level of warm-blooded organisms without either inhibiting or reducing the formation of cholesterol in the blood. Phytostenols, i.e. vegetable stenols, and esters thereof with fatty acids have already been proposed for this purpose by Peterson et al. in J. Nutrit. 50, 191 (1953). U.S. Pat. No. 3,089,939, U.S. Pat. No. 3,203,862 and DE-OS 2 035 069 (Procter & Gamble) also point in the same direction. The active substances are normally added to frying oils or edible oils and, accordingly, are absorbed through the food. However, the quantities used are generally minimal and, normally, amount to less than 0.5% by weight to prevent the edible oils from clouding or the stenols from precipitating on the addition of water. For use in food, in cosmetics, in pharmaceutical preparations and in the agricultural sector, storable emulsions of the stenol esters in sugar or polyglycerol esters are proposed in European patent application EP-A1 0 289 636 (Ashai). The incorporation of sitostanol esters in margarine, butter, mayonnaise, salad creams and the like for reducing the blood cholesterol level is proposed in European patent EP-B1 0 594 612 (Raision).

Unfortunately, a disadvantage of phytostenol esters is that, normally, they can only be added to foods in small quantities because otherwise they are in danger of affecting the taste and/or consistency of foods. However, if the blood cholesterol level is to be lastingly influenced, relatively large quantities of phytostenols or phytostenol esters would have to be absorbed. The rate at which the substances reduce serum cholesterol is also in need of improvement. Accordingly, the problem addressed by the present invention was to remedy these deficiencies.

DESCRIPTION OF THE INVENTION

The present invention relates to the use of mixtures of active substances for the production of hypocholesterolemic preparations, characterized in that
  (a) phytostenols and/or phytostenol esters and
  (b) potentiating agents selected from the group consisting of chitosans, phytostenol sulfates and/or (deoxy) ribonucleic acids are used.

It has surprisingly been found that chitosans, phytostenol sulfates and/or (deoxy)ribonucleic acids which, on their own, have very poor hypocholesterolemic properties, if any, act as potentiating agents for phytostenols and/or phytostenol esters, i.e. accelerate the reduction of the serum cholesterol level in the presence of phytostenols or phytostenol esters. In addition, when encapsulated in gelatine, both the phytostenols and/or phytostenol esters and the active-substance mixtures can readily be taken in by mouth.

Phytostenols and Phytostenol Esters

Phytostenols (also known as phytosterols) are vegetable steroids which only contain a hydroxyl group but no other functional groups at C-3. In general, phytostenols contain 27 to 30 carbon atoms and one double bond in the 5/6 position and occasionally in the 7/8, 8/9 or other positions. The corresponding saturated stanols, which are also encompassed by the present invention, can be obtained by hydrogenation from the unsaturated stenols. Typical examples of suitable phytostenols are ergostenols, campestenols, stigmastenols, brassicastenols and, preferably, sitostenols or sitostanols and, more particularly, β-sitostenols or β-sitostanols. Besides the phytostenols mentioned, their esters are preferably used. The acid component of the ester may go back to carboxylic acids corresponding to formula (I):

$$R^1CO\text{---}OH \tag{I}$$

in which $R^1CO$ is an aliphatic, linear or branched acyl group containing 2 to 22 carbon atoms and 0 and/or 1, 2 or 3 double bonds. Typical examples are acetic acid, propionic acid, butyric acid, valeric acid, caproic acid, caprylic acid, 2-ethyl hexanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeosteric acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids. Technical fatty acids containing 12 to 18 carbon atoms, for example cocofatty acid, palm oil fatty acid, palm kernel oil fatty acid or tallow fatty acid, are preferred. It is particularly preferred to use esters of β-sitostenol or β-sitostanol with fatty acids containing 12 to 18 carbon atoms. These esters may be prepared both by direct esterification of the phytostenols with the fatty acids or by transesterification with fatty acid lower alkyl esters or triglycerides in the presence of suitable catalysts, for example sodium ethylate or, more particularly, enzymes [cf. EP-A2 0195311 (Yoshikawa)].

Chitosans

Chitosans are biopolymers which to the group of hydrocolloids. Chemically, they are partly deacetylated chitins differing in their molecular weights which contain the following—idealized—monomer unit (II):

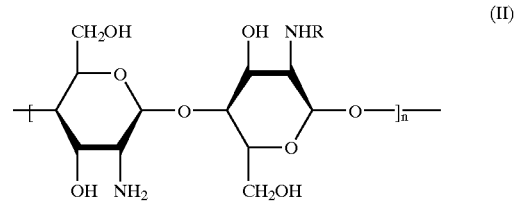

In contrast to most hydrocolloids, which are negatively charged at biological pH values, chitosans are cationic biopolymers under these conditions. The positively charged chitosans are capable of interacting with oppositely charged surfaces and are therefore used in cosmetic hair care and body-care products and pharmaceutical preparations (cf. Ullmann's Encyclopedia of Industrial Chemistry, 5th Ed., Vol. A6, Weinheim, Verlag Chemie, 1986, pages 231–332). Overviews of this subject have also been published, for example, by B. Gesslein et al. in HAPPI 27, 57 (1990), by O. Skaugrud in Drug Cosm. Ind. 148, 24 (1991) and by E.

Onsoyen et al. in Seifen-Öle-Fette-Wachse 117, 633 (1991). Chitosans are produced from chitin, preferably from the shell residues of crustaceans which are available in large quantities as inexpensive raw materials. In a process described for the first time by Hackmann et al., the chitin is normally first deproteinized by addition of bases, demineralized by addition of mineral acids and, finally, deacetylated by addition of strong bases, the molecular weights being distributed over a broad spectrum. Either low molecular weight chitosans with an average molecular weight of around 50,000 to around 250,000 dalton or high molecular weight chitosans with an average molecular weight of around 500,000 to around 2,000,000 are preferably used. Corresponding processes are known, for example, from Makromol. Chem. 177, 3589 (1976) or French patent application FR-A 2701266. Particularly preferred types are those which are disclosed in German patent applications DE-A1 4442987 and DE-A1 19537001 (Henkel) and which have an average molecular weight of 800,000 to 1,200,000 dalton, a Brookfield viscosity (1% by weight in glycolic acid) below 5,000 mPas, a degree of deacetylation of 80 to 88% and an ash content of less than 0.3% by weight. Besides the chitosans as typical cationic biopolymers, anionically or nonionically derivatized chitosans, such as for example the carboxylation, succinylation or alkoxylation products described, for example, in German patent DE-C2 3713099 (L'Oreal) and in German patent application DE-A1 19604180 (Henkel), may also be used for the purposes of the present invention.

Phytostenol Sulfates

Phytostenol sulfates are known substances which may be obtained, for example, by sulfation of phytostenols with a complex of sulfur trioxide and pyridine in benzene [cf. J. Am. chem. Soc. 63, 1259 (1941)]. Typical examples are the sulfates or ergostenols, campestenols, stigmastenols and sitostenols. The phyto-stenol sulfates may be used in the form of alkali metal and/or alkaline earth metal salts, ammonium, alkylammonium, alkanolammonium and/or glucam-monium salts. They are generally used in the form of their sodium salts.

(Deoxy)ribonucleic Acids (Deoxy)ribonucleic acids (DNA, RNA) are understood to be high molecular weight filament-like polynucleotides which are derived from 2'-deoxy-β-D-ribonucleosides or D-ribonucleosides which, in turn, are prepared from equivalent quantities of a nucleobase and the pentose 2-deoxy-D-ribofuranose or D-ribofuranose. The DNA or RNA may contain the purine derivatives adenine and guanine and the pyrimidines cytosine and thymine or uracil as nucleobases. In the nucleic acids, the nucleobases are attached by an N-glycosidic bond to carbon atom 1 of the ribose, so that adenosines, guanosines, cytidines and thimidines are formed in the particular individual case. In the acids, a phosphate group attaches the 5'-hydroxy group of the nucleosides to the 3'-OH group of the following phosphate group by a phosphodiester bridge to form single-stranded DNA or RNA. In view of the considerable length-to-diameter ratio, DNA or RNA molecules show a tendency towards strand breakage even under mechanical stressing, for example during extraction. For this reason, the molecular weight of the nucleic acids can reach $10^3$ to $10^9$ dalton. Concentrated DNA or RNA solutions, which are distinguished by liquid crystalline behavior, are used for the purposes of the invention. (Deoxy) ribonucleic acids which are obtained from marine sources, for example by extraction of fish sperm, and which have a molecular weight of 40,000 to 1,000,000 dalton are preferably used.

Commercial Applications

The active-substance mixtures according to the invention may contain the phytostenols and/or phytostenol esters and the potentiating agents in a ratio by weight of 99:1 to 1:99, preferably 90:10 to 10:90, more preferably 70:25 to 25:75 and most preferably 60:40 to 40:60, the only important requirement being to ensure that a quantity of component (a) sufficient to lower the blood cholesterol level is taken up through the use according to the invention. In one particular embodiment of the invention, the active-substance mixtures are encapsulated in known manner in gelatine, components (a) and (b) each being used in quantities of 0.1 to 50% by weight, preferably in quantities of 1 to 30% by weight, more preferably in quantities of 5 to 25% by weight and most preferably in quantities of 10 to 15% by weight, based on the weight of the gelatine capsules. Another aspect of the invention is the discovery that the encapsulation of the phytostenols and/or phytostenol esters in gelatine itself represents an advantageous embodiment for the oral administration of the active substances.

Another form of administration of the active-substance mixtures are suppositories which may be inserted rectally or vaginally and which may also contain gelatine, optionally in combination with glycerol, or even synthetic fats or waxes, polyethylene glycols or natural constituents, for example cocoa butter, as the suppository base.

The mixtures may also be dissolved or dispersed in normal foods, for example salad oils, dressings, mayonnaises, margarines, butter, frying fats, cocoa products, sausage and the like.

EXAMPLES

Examples 1 to 16, Comparison Examples C1 to C4

Gelatine capsules (weight ca. 1.5 g) containing 5% by weight and 10% by weight of β-sitostanol or β-sitostanol ester and optionally 5 or 10% by weight of the various potentiating agents and 0.5% by weight of radioactively labeled cholesterol were prepared. To investigate the hypocholesterolemic effect, male rats (each weighing ca. 200 g) were kept off food overnight. On the following day, a size-reduced gelatine capsule was inserted into each test animal with a little salt-containing water through a stomach probe. After 3, 6, 12, 24 and 48 h, blood was removed from the animals and the content of radioactive cholesterol was determined. The results—which represent the average value of the measurements of 10 test animals—are set out in Tables 1 and 2 below. The data relating to the reduction in radioactivity are based on a control group of test animals which were only given gelatine capsules containing 20% by weight of vitamin E and a corresponding quantity of radioactively labeled cholesterol. Mixtures 1 to 16 correspond to the invention while mixtures C1 to C4 are intended for comparison.

TABLE 1

Hypocholesterolemic effect (quantities in % by weight, based on gelatine capsule)

| Composition/activity | C1 | 1 | 2 | 3 | 4 | C2 | 5 | 6 | 7 | 8 |
|---|---|---|---|---|---|---|---|---|---|---|
| β-Sitostanol | 5 | 5 | 5 | 5 | 5 | 10 | 10 | 10 | 10 | 10 |
| Chitosan | — | 5 | — | — | — | — | 5 | — | — | — |
| β-Sitostenol sulfate sodium salt | — | — | 5 | — | — | — | — | 5 | — | — |
| Marine DNA (M = 150,000) | — | — | — | 5 | — | — | — | — | 5 | — |
| Radioactivity [%-rel] | | | | | | | | | | |
| After 3 h | 93 | 93 | 93 | 93 | 93 | 92 | 92 | 92 | 91 | 91 |

TABLE 1-continued

Hypocholesterolemic effect (quantities in % by weight, based on gelatine capsule)

| Composition/activity | C1 | 1 | 2 | 3 | 4 | C2 | 5 | 6 | 7 | 8 |
|---|---|---|---|---|---|---|---|---|---|---|
| After 6 h | 83 | 80 | 82 | 82 | 81 | 78 | 76 | 75 | 75 | 74 |
| After 12 h | 75 | 70 | 72 | 73 | 71 | 61 | 55 | 57 | 57 | 59 |
| After 24 h | 50 | 44 | 45 | 46 | 45 | 35 | 27 | 29 | 38 | 30 |
| After 48 h | 32 | 22 | 26 | 25 | 24 | 21 | 16 | 18 | 18 | 19 |

TABLE 2

Hypocholesterolemic effect (quantities in % by weight, based on gelatine capsule)

| Composition/activity | C3 | 9 | 10 | 11 | 12 | C4 | 13 | 14 | 15 | 16 |
|---|---|---|---|---|---|---|---|---|---|---|
| Lauric acid-β-sitostanol ester | 5 | 5 | 5 | 5 | 5 | 10 | 10 | 10 | 10 | 10 |
| Succinylated chitosan | — | 5 | — | — | — | — | 5 | — | — | — |
| Chitosan | — | — | 5 | — | — | — | — | 5 | — | — |
| β-Sitostenol sulfate sodium salt | — | — | — | 5 | — | — | — | — | 5 | — |
| Marine DNA (M-150,000) | — | — | — | — | 5 | — | — | — | — | 5 |
| Radioactivity [%-rel] | | | | | | | | | | |
| After 3 h | 95 | 94 | 94 | 94 | 94 | 93 | 91 | 91 | 91 | 91 |
| After 6 h | 84 | 83 | 83 | 83 | 82 | 79 | 80 | 76 | 76 | 75 |
| After 12 h | 76 | 71 | 72 | 72 | 72 | 62 | 60 | 58 | 57 | 58 |
| After 24 h | 51 | 44 | 45 | 45 | 46 | 34 | 31 | 29 | 39 | 29 |
| After 48 h | 30 | 28 | 25 | 26 | 25 | 20 | 20 | 17 | 17 | 18 |

What is claimed is:

1. A hypocholesterolemic composition comprising:
   (a) an active ingredient selected from the group consisting of a phytostenol, a phytostenol ester, and mixtures thereof; and
   (b) a potentiating agent selected from the group consisting of a chitosan, a (deoxy)ribonucleic acid, and mixtures thereof.

2. The composition of claim 1 wherein the active agent is selected from the group consisting of β-sitostenol, β-sitostanol, a β-sitostenol ester, a β-sitostanol ester, and mixtures thereof.

3. The composition of claim 1 wherein the β-sitostenol ester and β-sitostanol ester are formed using a carboxylic acid corresponding to formula (I):

$$R^1CO\text{—}OH \qquad (I)$$

wherein $R^1CO$ is an aliphatic, linear or branched alkyl group having from 2 to 22 carbon atoms, and up to 3 double bonds.

4. The composition of claim 3 wherein in formula (I), $R^1CO$ is an aliphatic, linear or branched alkyl group having from 12 to 18 carbon atoms.

5. The composition of claim 1 wherein the potentiating agent is a chitosan having an average molecular weight of from 50,000 to 2,000,000 dalton.

6. The composition of claim 1 wherein the potentiating agent is a succinylated chitosan.

7. The composition of claim 1 wherein the potentiating agent is a marine (deoxy)ribonucleic acid having an average molecular weight of from 40,000 to 1,000,000 dalton.

8. The composition of claim 1 wherein the active ingredient and potentiating agent are present in the composition in a ratio by weight of from 75:25 to 25:75.

9. The composition of claim 1 wherein the hypocholesterolemic composition is contained in a gelatine capsule.

10. The composition of claim 9 containing from 0.1 to 50% by weight of (a) and from 0.1 to 50% by weight of (b), all weights being based on the weight of the gelatine capsule.

11. A process for reducing serum cholesterol levels in warm-blooded organisms comprising administering an effective amount of a hypocholesterolemic composition to the warm-blooded organism, the hypocholesterolemic composition containing:
   (a) an active ingredient selected from the group consisting of a phytostenol, a phytostenol ester, and mixtures thereof; and
   (b) a potentiating agent selected from the group consisting of a chitosan, a (deoxy)ribonucleic acid, and mixtures thereof.

12. The process claim 11 wherein the active agent is selected from the group consisting of β-sitostenol, β-sitostanol, a β-sitostenol ester, a β-sitostanol ester, and mixtures thereof.

13. The process of claim 11 wherein the β-sitostenol ester and β-sitostanol ester are formed using a carboxylic acid corresponding to formula (I):

$$R^1CO\text{—}OH \qquad (I)$$

wherein $R^1CO$ is an aliphatic, linear or branched alkyl group having from 2 to 22 carbon atoms, and up to 3 double bonds.

14. The process of claim 13 wherein in formula (I), $R^1CO$ is an aliphatic, linear or branched alkyl group having from 12 to 18 carbon atoms.

15. The process of claim 11 wherein the potentiating agent is a chitosan having an average molecular weight of from 50,000 to 2,000,000 dalton.

16. The process of claim 11 wherein the potentiating agent is a succinylated chitosan.

17. The process of claim 11 wherein the potentiating agent is a marine (deoxy)ribonucleic acid having an average molecular weight of from 40,000 to 1,000,000 dalton.

18. The process of claim 11 wherein the active ingredient and potentiating agent are present in the composition in a ratio by weight of from 75:25 to 25:75.

19. The process of claim 11 wherein the hypocholesterolemic composition is administered orally, rectally or vaginally.

20. The process of claim 11 wherein the hypocholesterolemic composition is administered orally in a gelatine capsule containing from 0.1 to 50% by weight of (a) and from 0.1 to 50% by weight of (b), all weights being based on the weight of the gelatine capsule.

* * * * *